United States Patent [19]

Okumura et al.

[11] 4,358,626
[45] Nov. 9, 1982

[54] PROCESS FOR THE PRODUCTION OF SECONDARY ALCOHOLS

[75] Inventors: Yoshiharu Okumura, Kawagoe; Tadamori Sakakibara; Katsumi Kaneko, both of Ooi, all of Japan

[73] Assignee: Toa Nenryo Kogyo Kabushiki Kaisha, Tokyo, Japan

[21] Appl. No.: 290,491

[22] Filed: Aug. 6, 1981

[30] Foreign Application Priority Data

Dec. 25, 1980 [JP] Japan .............................. 55-182897

[51] Int. Cl.³ .............................................. C07C 29/04
[52] U.S. Cl. .................................... 568/899; 568/895; 568/896; 568/897; 568/898; 568/900; 568/901
[58] Field of Search ............... 568/895, 896, 897, 898, 568/899, 900, 901

[56] References Cited

U.S. PATENT DOCUMENTS

| | | | |
|---|---|---|---|
| 2,036,317 | 4/1936 | Bent et al. | 568/895 |
| 2,807,655 | 9/1957 | Pitwell | 568/897 |
| 2,813,908 | 11/1957 | Young | 568/895 |
| 3,006,970 | 10/1961 | Beuther et al. | 568/901 |
| 3,705,912 | 12/1972 | Massie | 568/901 |
| 3,989,762 | 11/1976 | Ester et al. | 260/641 |
| 3,994,983 | 11/1976 | Webers et al. | 260/641 |
| 4,060,564 | 11/1977 | Kanemaru et al. | 568/898 |
| 4,131,750 | 12/1978 | Minachev et al. | 568/901 |
| 4,150,245 | 4/1979 | Sommer et al. | 568/896 |
| 4,214,107 | 7/1980 | Chang et al. | 568/897 |
| 4,284,831 | 8/1981 | Okumura et al. | 568/896 |

FOREIGN PATENT DOCUMENTS

| | | |
|---|---|---|
| 1201181 | 8/1970 | United Kingdom . |
| 1311172 | 3/1973 | United Kingdom . |
| 1374368 | 11/1974 | United Kingdom . |
| 1500667 | 2/1978 | United Kingdom . |
| 1518461 | 7/1978 | United Kingdom . |

OTHER PUBLICATIONS

Related Application Mentioned: U.S. Serial No. 146,443 filed May 5, 1980–allowed Feb. 11, 1981.
Table "Recent Japanese Patents on Heterogenous Direct Hydration of n-Olefins".

Primary Examiner—Joseph E. Evans
Attorney, Agent, or Firm—Rebecca Yablonsky

[57] ABSTRACT

Secondary alcohols are produced by the hydration of a n-olefin substantially free from an isoolefin in the presence as catalyst of an acidic cation exchange resin such as a sulfonated styrene-divinylbenzene copolymer and in the presence of an oxy acid or lactone thereof such as γ-valerolactone. The process is especially useful for hydrating a n-butene feed or a feed consisting essentially of n-butenes and butane to produce secondary butyl alcohol.

9 Claims, 1 Drawing Figure

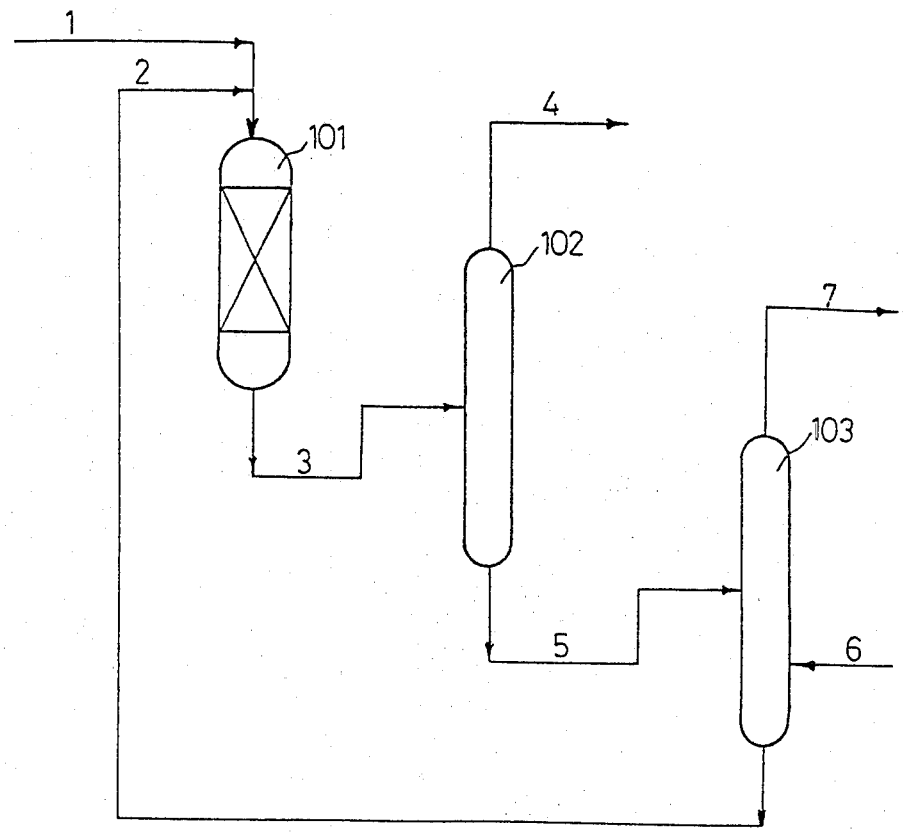

PROCESS FOR THE PRODUCTION OF SECONDARY ALCOHOLS

This invention relates to a process for producing a secondary alcohol by hydrating in a heterogeneous system a n-olefin or a hydrocarbon mixture containing a n-olefin to the corresponding secondary alcohol.

BACKGROUND OF THE INVENTION

Heretofore there have been known as processes for producing alcohols an indirect hydration process in which an olefin is absorbed by sulfuric acid and the resulting sulfuric acid ester is hydrolyzed to obtain an alcohol; and a direct hydration process which utilizes a solid acid or an aqueous acid solution, for example a process of hydration of an olefin which utilizes a solid acid especially a cation exchange resin as a catalyst and a sulfone as a reaction solvent (British Pat. No. 1,518,461).

SUMMARY OF THE INVENTION

Applicants have made various studies to find an effective solvent for hydration of n-olefins which utilizes a solid acid, especially a cation exchange resin, as a catalyst.

Accordingly, this invention is a process for producing a secondary alcohol by hydrating a n-olefin or a hydrocarbon mixture containing a n-olefin in the presence of a solid catalyst, which process for producing a secondary alcohol is characterized in that a hydroxy acid or a derivative thereof is present.

The n-olefin or the hydrocarbon mixture containing a n-olefin (which contains no or, if any, a relatively small amount of an isoolefin) to be used in this invention is an alpha olefin or an olefin with an internal double bond having 3 or more carbon atoms, suitably a monoolefinic hydrocarbon having 3–12 carbon atoms, preferably 3–8 carbon atoms, or a hydrocarbon mixture containing the same. For example, there may be mentioned propylene, butenes, pentenes, hexenes, heptenes, octenes, or hydrocarbons containing them, among which propylene, butene-1 or butene-2 is especially useful for hydration.

As for the starting material, butenes, C₄ hydrocarbon fractions obtained industrially by steam cracking, catalytic cracking etc. of petroleum fractions are employed, but generally a mixture of butanes and butenes obtained by separating and removing isobutylene from the above C₄ fractions or a hydrocarbon having a small content of isobutylene is preferably employed, that is to say, a hydrocarbon or C₄ fraction substantially free from isobutylene. Secondary butanol is of particular importance for the synthesis of methyl ethyl ketone or as a solvent or for other uses.

BRIEF DESCRIPTION OF THE DRAWING

The accompanying drawing is a flow diagram which illustrates carrying out the process of the present invention continuously.

DETAILED DESCRIPTION

The oxy acid or derivative thereof used in the present invention is illustrated in the following:

Examples of the oxy acid are $C_2$–$C_5$ oxy acids such as oxyacetic acid ($HOCH_2COOH$), lactic acid ($CH_3CH(OH)COOH$), 3-oxypropionic acid ($HOCH_2CH_2COOH$), β,β,β-trichlorolactic acid ($Cl_3CCH(OH)COOH$), oxypivalic acid ($HOCH_2C(CH_3)_2COOH$), γ-oxybutryic acid ($HOCH_2CH_2CH_2COOH$) and the like.

As a typical example of the derivative of hydroxy acids, lactones corresponding to the intramolecularly condensed hydroxy acids are preferable, but other oxy acid esters may be used particularly the lower alkyl esters such as the methyl and ethyl esters. Useful examples of the lactone include β-propiolactone

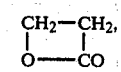

β,β-dimethylpropiolactone

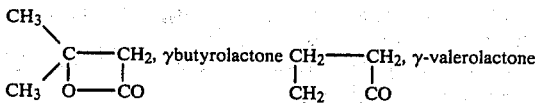

γbutyrolactone, γ-valerolactone

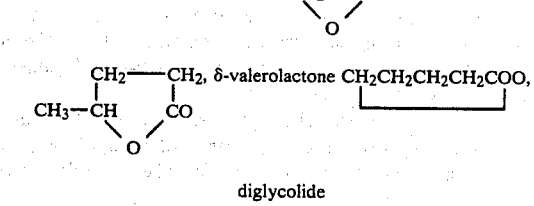

δ-valerolactone, $CH_2CH_2CH_2CH_2COO$, diglycolide lactide

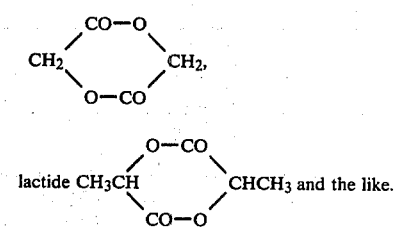

and the like.

Useful examples of the oxy acid esters are glycolic acid methyl ester $HOCH_2COOCH_3$, glycolic acid ethyl ester $HOCH_2COOC_2H_5$ and the like. Thus the oxy acids particularly of $C_2$–$C_5$, straight or branched-chain alkyl type, and the derivatives thereof, viz., the oxy acid lower alkyl esters, the lactones, lactides, the halogen, especially chlorine, substituted derivatives, or mixtures of these, may be employed.

The oxy acid or derivative thereof is ordinarily used in the form of a solution in water, but it is not always required that it should be completely dissolved therein. As the added quantity of the oxy acid or derivative thereof is increased, in general, the rate of formation of secondary alcohol increases but if too large an excess is added, the efficiency of the reactor is lowered. Accordingly, the said compound is generally added in a proportion of 0.5 to 100 parts, preferably 1 to 20 parts by weight, to 1 part by weight of water.

The solid catalyst used in the present invention includes preferably strongly acidic cation exchange resins, for example, sulfonated polystyrene resins in which sulfonic acid groups are introduced into a base of a copolymer of styrene and divinylbenzene; phenolsulfonic acid resins in which sulfonic acid groups are introduced into a condensate of phenol and formaldehyde; and perfluorosulfonic acid resins consisting of copolymers of sulfonated vinyl ether fluoride and fluorocarbon, which are preferably of a gel type, macroporous type or macroreticular type. Supported ion exchange resins may be used. In addition, other solid catalysts for hydration can be used, for example, oxide type catalysts such as alumina, silica alumina, silica gel, zeolites, mordenites, kaolin; oxides of metals such as tungsten, thorium, zirconium, molybdenum, zinc, titanium and chromium; supported ones of these oxides; mineral acid catalysts such as supported phosphoric acid; heteropoly acid catalysts such as supported silicotungstic acid; sulfides such as sulfides of nickel and nickel-tungsten or supported ones of these sulfides.

The quantity of the catalyst depends upon how it is used, that is, whether it is used in the form of a suspension or a fixed bed. In the former case, the quantity of the catalyst is preferably 0.5 to 20% by weight of an aqueous solution of an oxy acid or derivative thereof.

The molar ratio of water to the n-olefin ranges preferably from 1 to 10 since if less than 1, the degree of conversion is reduced, while if too large, the efficiency of the reactor is lowered.

The reaction temperature is suitably 50° to 200° C., preferably 80° to 170° C.

As regards the reaction pressure, it is preferred to operate under such pressure that the reaction system is maintained in the liquid phase or the gas-liquid phase, generally 10–100 kg/cm$^2$G.

Although the reactor may be a batch type, the reaction is generally operated on a continuous basis using a fixed bed of a solid catalyst, preferably an acid type cation exchange resin.

The reaction time is suitably in the range of 2 minutes to 20 hours for a batch method, and in the range of 0.1–10 vol/hr/vol expressed as the liquid hourly space velocity (LHSV) of the hydrocarbon in a continuous operation.

One embodiment of the process of the present invention in which a n-olefin in a hydrocarbon mixture containing this n-olefin is continuously hydrated and the obtained corresponding alcohol is separated, is described with reference to the accompanying drawing. A starting hydrocarbon and an aqueous solution of a hydroxy acid or a derivative thereof are supplied to a hydration reactor 101 packed with a catalyst via line 1 and line 2, respectively. The reaction mixture is withdrawn by line 3 and introduced into an unreacted hydrocarbon separating distillation column 102, to separate the unreacted hydrocarbon via line 4, while said aqueous solution containing an alcohol is withdrawn by line 5 and introduced into an alcohol separating distillation column 103. Steam is supplied from a line 6, the aqueous alcohol solution is separated by line 7, and said aqueous solution is separated from the column bottom and recycled to the reactor. Removal of water from the aqueous alcohol solution is achieved in a conventional manner.

This invention remarkably improves the rate of hydration reaction of a n-olefin and the degree of conversion thereof and thus can produce the corresponding secondary alcohol in high yield.

The following examples and comparative examples are provided to more particularly describe this invention. In these examples and comparative examples, all the percents are mole percents.

EXAMPLES 1–8

In a stainless steel autoclave equipped with a stirrer and 35 g each of a cation exchange resin, viz., a sulfonated styrene-divinylbenzene copolymer (exchange capacity: 4.8 meq/g, surface area: 35 m$^2$/g) as a catalyst, hydration reactions of propylene, butene-1 and butene-2, respectively, were conducted, each employing the aqueous solution of the hydroxy acid or derivative thereof indicated under the conditions given in Table 1. After each reaction, the reaction product was quenched and was analyzed by gas chromatography to determine the corresponding alcohol and by-products. The results are set forth in Table 1.

TABLE 1

| Ex. | Starting Material Hydrocarbon Kind | Volume (ml) | Hydroxy Acid or a Derivative thereof Kind | Volume (ml) | Water (ml) | Reaction Temp. (°C.) | Reaction Pressure (kg/cm$^2$G) | Reaction Time (hr) | Yield of the Secondary Alcohol (%) | Yield of By-products (%) |
|---|---|---|---|---|---|---|---|---|---|---|
| 1 | Butene-1 | 200 | γ-Hydroxylactic acid | 300 | 200 | 110 | 30 | 10 | 11.1 | 0.2 |
| 2 | Butene-1 | 200 | δ-Valerolactone | 600 | 400 | 140 | 50 | 5 | 24.7 | 0.5 |
| 3 | Butene-1 | 200 | 3-Hydroxypropionic acid | 1500 | 1000 | 140 | 50 | 5 | 23.1 | 0.2 |
| 4 | trans Butene-2 | 200 | γ-Butyrolactone | 400 | 100 | 140 | 50 | 5 | 31.2 | 0.5 |
| 5 | cis Butene-2 | 200 | γ-Butyrolactone | 350 | 150 | 140 | 50 | 5 | 27.8 | 0.5 |
| 6 | Propylene | 200 | γ-Hydroxylactic acid | 400 | 100 | 140 | 100 | 5 | 48.4 | 0.7 |
| 7 | Butene-1 | 200 | γ-Valerolactone | 300 | 200 | 140 | 50 | 5 | 22.8 | 0.4 |
| 8 | Butene-1 | 200 | γ-Butlrolactone | 450 | 50 | 140 | 50 | 5 | 35.6 | 0.6 |

COMPARATIVE EXAMPLES 1–5

In hydration reactions of butene-1 and propylene respectively, employing the reactor and catalyst similar to those in the examples, comparative experiments were conducted where a hydroxy acid or a derivative thereof was not added to the reaction system. The conditions and results of the experiments are given in Table 2.

The yields of the secondary alcohols and by-products were determined similarly as in the examples.

COMPARATIVE EXAMPLE 6

An experiment was conducted in a similar manner as in Example 7 except that the γ-valerolactone in Example 7 was replaced by sulfolane. The results are given in Table 2.

COMPARATIVE EXAMPLE 7

An experiment was conducted in a similar manner as in Example 8 except that the γ-butyrolactone in Example 8 was replaced by sulfolane. The results are given in Table 2.

TABLE 2

| Comparative Example | Starting Material Hydrocarbon Kind | Volume (ml) | Solvent Kind | Volume (ml) | Water (ml) | Reaction Temp. (°C.) | Reaction Pressure (kg/cm²G) | Reaction Time (hr) | Yield of the Secondary Alcohol (%) | Yield of By-products (%) |
|---|---|---|---|---|---|---|---|---|---|---|
| 1 | Butene-1 | 200 | — | — | 200 | 110 | 30 | 10 | 6.9 | 1.2 |
| 2 | Butene-1 | 200 | — | — | 200 | 140 | 50 | 5 | 14.2 | 2.2 |
| 3 | Butene-1 | 200 | — | — | 500 | 140 | 50 | 5 | 14.5 | 2.1 |
| 4 | Butene-1 | 200 | — | — | 1000 | 140 | 50 | 5 | 8.1 | 1.5 |
| 5 | Propylene | 200 | — | — | 500 | 140 | 100 | 5 | 25.1 | 3.8 |
| 6 | Butene-1 | 200 | Sulfolane | 300 | 200 | 140 | 50 | 5 | 12.3 | 0.4 |
| 7 | Butene-1 | 200 | Sulfolane | 450 | 50 | 140 | 50 | 5 | 25.7 | 0.7 |

EXAMPLE 9

In this example a process is described in which n-butene in a $C_4$ hydrocarbon mixture was continuously hydrated and the corresponding secondary butyl alcohol (hereinafter referred to as SBA) was separated and recovered using the device as illustrated in the drawing.

To the hydration reactor 101 were supplied the starting material hydrocarbon mixture (20% of butanes, 48% of butene-1 and 32% of butene-2) via line 1 at a rate of 125 moles/hr and an aqueous solution of γ-butyrolactone (41.2% of γ-butyrolactone) via line 2 at a rate of 405 moles/hr. The hydration reactor 101 had been packed with a cation exchange resin composed of a copolymer of styrene and divinylbenzene (exchange capacity: 4.9 meq/g, surface area: 45 m²/g) and was maintained under conditions of a temperature of 140° C., a pressure of 50 kg/cm² G and a LHSV of 1 vol/hr/vol. The reaction mixture was withdrawn by line 3 and fed to the unreacted hydrocarbon separating distillation column 102, from which the unreacted hydrocarbon (41.7% of butanes and 58.3% of n-butenes) was separated via line 4 at the column top at a rate of 60 moles/hr. The aqueous γ-butyrolactone phase containing SBA withdrawn by line 5 at the bottom was supplied to the SBA separating distillation column 103 at a rate of 404 moles/hr, while steam was supplied thereto from line 6 on the lower side at a rate of 165 moles/hr, and the crude SBA (having an SBA content of 39.0%) was separated by line 7 at the column top at a rate of 164 moles/hr. The aqueous γ-butyrolactone phase separated from the column bottom was recycled to the hydration reactor 101 via line 2. The yield of SBA based on n-butene in the starting hydrocarbon was 64% and the yield of by products was 1%.

What is claimed is:

1. In a process for the production of secondary alcohols by hydrating a n-olefin selected from the group consisting of propylene and n-butene or a hydrocarbon mixture containing said n-olefin with water in the presence of an acidic cation exchange resin catalyst, the improvement which comprises using a feed which is substantially free from an isoolefin and carrying out the reaction in the presence of a $C_2$ to $C_5$ oxy acid or the lactones, lactides, methyl or ethyl esters thereof, or mixtures thereof in a proportion of 0.5 to 100 parts by weight to 1 part by weight of water.

2. The process according to claim 1 in which the oxy acid is selected from the group consisting of oxy-acetic acid, lactic acid, 3-oxypropionic acid, β,β,β-trichlorolactic acid, oxypivalic acid and γ-oxybutyric acid.

3. The process according to claim 1 in which the lactone is selected from the group consisting of β-propiolactone, β,β-dimethylpropiolactone, γ-butyrolactone, γ-valerolactone and δ-valerolactone.

4. The process according to claim 1 in which the lactide is selected from the group consisting of diglycolide and lactide.

5. The process according to claim 1 in which the oxy acid ester is selected from the group consisting of glycolic acid methyl ester and glycolic acid ethyl ester.

6. The process according to claim 1 in which the resin is a sulfonated resin.

7. The process according to claim 6 in which the resin is a sulfonated styrene-divinylbenzene copolymer.

8. The process according to claims 1, 6 or 7 in which the feed contains butene-1 and/or butene-2 and secondary butyl alcohol is recovered as product.

9. The process according to claim 8 in which the feed consists essentially of n-butenes and butane.

* * * * *